United States Patent [19]

Demay

[11] 4,306,086
[45] Dec. 15, 1981

[54] HYDROFORMYLATION CATALYST SYSTEM AND PROCESSES

[75] Inventor: Claude Demay, Voisins Le Bretonneux, France

[73] Assignee: Chimiques Ugine Kuhlmann, Courbevoie, France

[21] Appl. No.: 157,501

[22] Filed: Jun. 9, 1980

[30] Foreign Application Priority Data

Jun. 22, 1979 [FR] France ................. 79 16096

[51] Int. Cl.$^3$ ............... C07C 45/50; B01J 31/24; B01J 31/40
[52] U.S. Cl. ................. 568/454; 252/411 R; 252/412; 252/431 P
[58] Field of Search ............... 252/414, 412, 413, 420, 252/411 R, 411 S, 431 P, 431 C, 428; 568/454

[56] References Cited

U.S. PATENT DOCUMENTS

| 3,239,566 | 3/1966 | Slaugh et al. | 568/454 |
|---|---|---|---|
| 3,576,881 | 4/1971 | Senn, Jr. | 252/431 P |
| 3,976,703 | 8/1976 | Wilkes | 568/451 |
| 4,200,592 | 4/1980 | Hignett et al. | 568/454 |
| 4,221,743 | 9/1980 | Halstead et al. | 568/454 |
| 4,230,641 | 10/1980 | Bartish | 568/454 |
| 4,262,141 | 4/1981 | Richter | 568/454 |

FOREIGN PATENT DOCUMENTS

| 854403 | 11/1977 | Belgium . | |
|---|---|---|---|
| 1300404 | 6/1962 | France . | |
| 2357511 | 2/1978 | France . | |
| 2377991 | 8/1978 | France . | |
| 2377992 | 8/1978 | France . | |
| 2395246 | 1/1979 | France . | |
| 98500 | 7/1961 | Netherlands . | |
| 1385475 | 2/1975 | United Kingdom | 568/454 |

Primary Examiner—P. E. Konopka
Attorney, Agent, or Firm—Sigalos & Levine

[57] ABSTRACT

This invention relates to a catalyst system for the hydroformylation of propene consisting essentially of a catalytic complex of rhodium, carbon monoxide, and a triarylphosphine, and a cobalt compound; to the process for stabilizing and/or regenerating a catalyst complex combination of rhodium, carbon monoxide, and a triarylphosphine comprising adding a cobalt compound to said catalyst complex; and to the process of hydroformylating propene with said catalyst system.

9 Claims, No Drawings

HYDROFORMYLATION CATALYST SYSTEM AND PROCESSES

BACKGROUND OF THE INVENTION

The methods of hydroformylation of an olefin to prepare aldehydes or alcohols having one more carbon atom than the initial olefin consist in reacting this olefin with a synthesis gas in the presence of a complex catalyst containing a metal selected from the series of transition metals. Of the latter, the metals in group VIII of the Periodic Table, namely, iron, cobalt, nickel, ruthenium, rhodium, palladium, osmium, iridium and platinum are used, in particular.

These metals may be used in the form of carbonyl metals, but it is known that complex combinations which contain at least one biphyllic ligand such as a phosphine in addition to the metal and carbon monoxide yield more linear products and make it possible to work at lower pressures. Such combinations are described, for example, in French Pat. No. 1,300,404 and U.S. Pat. No. 3,239,566.

The process may be carried out by introducing, into a reaction zone, a supply stream made up of a mixture of hydrogen and carbon monoxide, the olefinic charge which is to be hydroformylated, and the recycled catalyst, dissolved in a solvent or in the heavy reaction products. The reaction product may be recovered from the reaction medium by distilling a liquid current continuously drawn off from the reactor, while the heavy products containing the catalyst are recycled as mentioned above.

The reaction products may also be recovered by extracting them directly from the reaction medium by entraining them in a current of gas leaving the reaction zone; this gas may, for example, be excess systhesis gas. This process has the advantage of leaving the catalytic system where it is, but it can only conveniently be used for the hydroformylation of light olefins such as propene, butenes or pentenes.

In the particular case of the hydroformylation of propene, any one of these methods may be chosen.

Of the catalytic systems mentioned hereinbefore, one of those which gives the best results and has therefore been widely developed on an industrial scale is made up of a catalyst containing rhodium in a complex combination with carbon monoxide and a triarylphosphine. For a system of this kind, it is advantageous, particularly for obtaining good selectivity in linear products, to use high molar ratios of phosphorus to rhodium, these ratios having a minimum value of 10.

Hydroformylation of propene is generally effected at a temperature between about 60° C. and 150° C., temperatures of between 80° C. and 125° C. being most frequently used. The total pressure of hydrogen and carbon monoxide is fairly low, between about 1 to 40 bars, and the molar ratio $H_2/CO$ is between about 1/1 and 20/1.

Under these conditions of hydroformylation, the activity of the catalyst is found to decrease in the course of time. This decrease may be fairly slight, less than a few percent of the initial activity, per day, but it increases with the temperature, and under certain conditions there may be reductions in the catalytic activity of several dozen percent after a few hours of reaction. This phenomenon is extremely troublesome, as in every case it means that, sooner or later, the catalytic charge has to be replaced or re-treated.

It is known that certain products adversely affect (are "poisons" to) hydroformylation catalysts. This is true of certain compounds containing sulphur such as COS, $H_2S$, thioethers, mercaptans, and the like, or halogens such as chlorine, for example. These compounds are cited, in particular, in Jurgen Falbe's book "Carbon Monoxide in Organic Synthesis", Springer-Verlag, New York, 1970, or in French Pat. No. 2,377,991. When carrying out a hydroformylation reaction, obviously attempts are made to eliminate these poisons from the catalyst. They may be introduced by the olefin which is to be hydroformylated or by the synthesising gas. However, it is found that, in spite of taking every precaution to avoid introducing any detectable trace of these poisons into the reaction medium, the activity of rhodium/triphenylphosphine catalytic systems as described hereinbefore decreases in the course of time.

This phenomenon is described in French Pat. No. 2,377,992, but its causes are still not fully understood. It might be supposed that undectectable traces of poisons, such as those mentioned hereinbefore, may reduce the activity of the catalyst, by an accumulative effect, particularly if the catalyst is kept in the reactor when the reaction products are drawn off in the gaseous phase. It might also be thought that this phenomenon is due to the slow, irreversible development of the catalytic complexes to inactive types, or to the formation of organic molecules capable of combining with the rhodium to form inactive complexes.

Although the cause or causes of this phenomenon are still not fully known, numerous solutions have been proposed to remedy it. In French Pat. No. 2,357,511 it is stated that the deactivated catalytic system returns to its initial activity when traces of oxygen are admitted into the reactor. According to French Pat. No. 2,377,991, the stability of the catalytic system is improved by adding an alkyl-diarylphosphine to the triphenylphosphine; or again, according to Belgian Pat. No. 854,403, the deactivation of the catalyst is attributed to the formation of ill-defined heavy products. These harmful compounds are eliminated by continuous intense stripping of the reaction medium.

SUMMARY OF THE INVENTION

The present invention provides a simple and effective means of reducing and even preventing the loss of catalytic activity of the catalyst during the hydroformylation of propene.

Briefly, the present invention relates to a catalyst system for the hydroformylation of propene consisting essentially of a catalytic complex of rhodium, carbon monoxide, and a triarylphosphine and a cobalt compound free of any group likely to adversely affect the hydroformylation reaction.

The invention also comprises the process of stabilizing or regenerating the hydroformylation catalyst for propene, said catalyst consisting essentially of a catalytic complex of rhodium, carbon monoxide, and a triarylphosphine, comprising adding to said catalytic complex a cobalt compound free of any group likely to adversely affect the hydroformylation reactor.

Further, the invention comprises the improvement in the process of hydroformylating propene with a catalytic complex consisting essentially of rhodium, carbon monoxide, and a triarylphosphine, the improvement comprising adding a cobalt compound to the reaction medium during the hydroformylation, said cobalt compound being free of any group likely to adversely affect the hydroformylation reaction.

DETAILED DESCRIPTION

It must be stated at the outset that the precise reasons for the unexpected effects of cobalt in the present invention are not completely understood or known. Cobalt is known as the basis for a number of complexes which are active in hydroformylation, but under operating conditions such as those mentioned hereinbefore; i.e., at low temperatures and at low pressures for the synthesising gas, cobalt has virtually no activity as a hydroformylation catalyst and consequently the resulting products are comparable to those which could have been obtained in the absence of cobalt.

In the instant invention, the advantageous properties of reactions catalyzed by complex combinations of rhodium, carbon monoxide and triarylphosphine are retained, namely good selectivity for linear aldehydes and the formation of only small amounts of heavy products.

The rhodium, carbon monoxide, and particular triarylphosphine used can be any conventionally used in preparing hydroformylation catalysts for propene and, moreover, they can be used in any of the known and conventional proportions as more particularly set forth in the book and patents set forth above.

The quantities of cobalt used to form the catalyst system are not critical since, as mentioned above, cobalt does not act directly as a hydroformylation catalyst and therefore does not compete with the rhodium in its advantages. For this reason, atomic ratios of Co to Rh of 100 or more can be used, for example. When a substantial amount of rhodium is used in the reaction, the use of high ratios of Co to Rh may lead to some complexes being insoluble in the reaction medium. This upper limit for the permissible cobalt content depends chiefly on the nature of the solvent which is used and the temperature at which the reaction takes place. In practice, one skilled in this art can readily determine this solubility limit which should not be exceeded, for each particular case, experimentally without any special effort. Similarly, there is no lower limit for the Co/Rh ratio, as the stabilization effect, or regeneration effect in the case of a used catalytic system, is already considerable for Co/Rh ratios as low as 1/100. In practice, owing to the relatively low price of cobalt compared with the price of rhodium, atomic ratios of Co/Rh of between 50/1 and 1/10 are used, with which satisfactory results are obtained.

The cobalt may be added effectively to the reaction medium in extremely varied forms. The majority of combinations containing cobalt can be used to obtain the desired stabilizing or regenerating effects. For example, the cobalt may be introduced in carbonyl form, such as $Co_2(CO)_8$, $HCo(CO)_4$; the colbalt may also be used in the form of an inorganic salt such as, for example, cobalt sulphate; or in the form of an organic salt such as cobalt acetate, cobalt benzoate, cobalt naphthenate or cobalt acetylacetonate; or mixtures thereof. However, the cobalt compound used should not contain any group likely to adversely affect (be poisonous to) the oxo reaction itself. Thus, when the cobalt is introduced in the form of cobalt chloride, the reaction is blocked, but, as stated above, chlorine is well known to be a poison to the oxo reaction.

When the cobalt is used in a carbonyl form, regeneration of a used catalytic system occurs almost immediately. On the other hand, when it is used in the form of an organic or inorganic salt, the regenerating effect does not occur until after a generally longer period of time, which may be several hours, depending on the conditions. In view of this finding, it may therefore be hypothesized that the cobalt forms a complex combination with the carbon monoxide and the phosphine, regardless of the form in which the cobalt is introduced. This remark, which is intended to attempt to explain the phenomenon observed, does not, by any means, constitute a limit to the scope of this invention, for which other explanations are, of course, still possible.

A unique advantage of the present invention is that the cobalt compound can be added to the catalytic complex of rhodium, carbon monoxide, and a triarylphosphine to form the catalyst system before the hydroformylation reaction; it can be added to the reaction medium containing said catalytic complex during hydroformylation; or it can be added to said catalytic complex after it has lost some of its initial activity.

In the first and second cases it stabilizes the catalyst system and reduces or even prevents the loss of catalytic activity. In the second case it can also regenerate the catalyst so that it requires a degree of activity comparable to its initial activity; something that also occurs in the third case.

The invention will be further described in connection with the following examples set forth for purposes of illustration only.

EXAMPLE 1

This example is given as a comparison to illustrate the degradation of the catalyst over a period of time.

20 cm$^3$ of n-butyraldehyde, 43 mg of rhodium hydridocarbonyl tris-triphenylphosphine, and 1.33 g of triphenylphosphine are placed in a 200 ml autoclave fitted with a stirrer, a temperature sensor and a pipe for a supply of gas. After the autoclave has been closed and stirring has started, the autoclave is heated to reach a temperature of 125° C. in 90 minutes. The relative pressure is 3.9 bars at this moment. The following partial pressures are then established in the autoclave:

| Propene | 2 bars |
|---|---|
| Carbon monoxide | 0.7 bars |
| Hydrogen | 5.5 bars |

The total relative pressure, which attains 12.1 bars, is maintained at this level by continuously adding a mixture of CO/H$_2$/propene gas in the ratios 1/1/1. The following gas consumptions are then recorded:

| 0–15 minutes | 1.10 N liter |
|---|---|
| 60–75 minutes | 0.80 N liter | representing a loss of activity in the catalytic system of 27% in 1 hour.

EXAMPLE 2

Example 1 is repeated except that 8.1 mg of dicobalt octacarbonyl, Co$_2$(CO)$_8$, are added at the same time as the catalyst rhodium hydridocarbonyl tris-triphenylphosphine. Thus, at 125° C. the following gas consumptions are recorded:

| | |
|---|---|
| 0–15 minutes | 1.35 N liter |
| 15–30 minutes | 1.95 N liter |
| 60–75 minutes | 2.22 N liters |

EXAMPLE 3

This example is given as a comparison to illustrate the ineffectiveness of the cobalt as a catalyst.

The same test as in Example 2 is repeated, except that the catalyst is not added.

After 3 hours at 125° C., the gas consumption is less than 0.02 N liter.

EXAMPLE 4

A hydroformylation reaction of propene is carried out in the presence of 86 mg of rhodium hydridocarbonyl tris-triphenylphosphine and 2.7 g of triphenylphosphine under the same conditions as in example 1, except that the temperature is maintained at 105° C. The following gas consumptions are recorded:

| | |
|---|---|
| 0–15 minutes | 0.80 N liter |
| 120–135 minutes | 0.65 N liter |
| 240–255 minutes | 0.58 N liter |

EXAMPLE 5

Example 4 is repeated, but after 255 minutes, after cooling and releasing the pressure, 36.8 ml of liquid are drawn off from the autoclave, which are then adjusted to 40 ml and divided into two equal portions of 20 ml.

8.1 mg of $Co_2(CO)_8$ are then added to one of the portions.

Three hydroformylation reactions are then carried out at 95° C. using, as the starting catalytic solutions, the two previous solutions, on the one hand, and a freshly prepared catalytic solution of 20 ml of n-butyraldehyde in which 43 mg of rhodium hydridocarbonyl tris-triphenylphosphine and 1.55 g of triphenylphosphine have been dissolved, on the other hand. Otherwise, the conditions of hydroformylation are identical to those in Example 1. The following results were obtained:

| | Catalytic solution aged for 255 minutes at 105° C. | | |
|---|---|---|---|
| | As is | With addition of 8.1 mg of $Co_2(CO)_8$ | Solution of new catalyst As is |
| Productivity in butanals at 95° C. (g/hour × g of rhodium) | 400 | 530 | 520 |
| Linearity of butyraldehydes produced | 89.9 | 90.1 | 90 |

EXAMPLE 6

Hydroformylation tests are carried out at 125° C. under the same conditions as in Example 1, but adding cobalt in various forms to the reaction medium.

In every case, the atomic ratio of Co to Rh was maintained equal to one.

Test 1 gives, as a comparison, the result obtained with the catalyst with no cobalt according to Example 1.

| Test no. | Combination containing the cobalt | Average productivity in butanals at 125° C. for 75 minutes in g/hour × g of rhodium |
|---|---|---|
| 1 | — | 735 |
| 2 | cobalt acetate $Co(CH_3COO)_2 \cdot 4H_2O$ | 1,150 |
| 3 | cobalt II acetylacetonate | 1,490* |
| 4 | cobalt III acetylacetonate | 1,570** |
| 5 | cobalt naphthenate | 1,530 |
| 6 | cobalt sulphate $CoSO_4 \cdot 7H_2O$ | 1,070 |

*Apart from 15 minute induction period
**Apart from 60 minute induction period

EXAMPLE 7

This example demonstrates the effect of a cobalt compound on a spent catalyst.

500 ml of n-butyraldehyde,
1.1 g of rhodium hydridocarbonyl tris-triphenylphosphine, and
33 g of triphenylphosphine are introduced into a two liter autoclave with a stirrer, fitted with a temperature sensor, a pipe for supplying gas and a pipe for drawing off the liquid; this autoclave having been purged with argon.

After sealing the autoclave, the temperature is brought to 95° C. and the following partial pressures are then established:

| | |
|---|---|
| propene | 2 bars |
| carbon monoxide | 1 bar. |

20 cm³ batches are drawn off after 168, 192, 315, 365, and 390 hours of treatment. With the exception of the sample taken after 168 hours, which is used as a control, a cobalt compound is added to each of the other samples, in the form and atomic ratio Co/Rh defined in the Table hereinafter.

With each of these catalytic compositions, hydroformylation reactions are carried out in the apparatus according to Example 1, under the following conditions:

| | |
|---|---|
| temperature of hydroformylation | 95° C. |
| partial pressures of: | |
| propene | 2 bars |
| carbon monoxide | 0.7 bars |
| hydrogen | 5.5 bars |

The following results are obtained:

| Test no. | Aging Time in hours | Cobalt compound added | Activity: Average productivity in butanals at 95° C. for 75 minutes in g/hour × g of Rh |
|---|---|---|---|
| 1 | 168 | Nil | 265 |
| 2 | 192 | Cobalt acetate Co/Rh = 1 | 660 |
| 3 | 315 | $Co_2(CO)_8$ Co/Rh = 10 | 690 |
| 4 | 365 | Cobalt acetate Co/Rh = 0.3 | 610 |
| 5 | 390 | $CO_2(CO)_8$ Co/Rh = 1 | 620 |

It is found that the catalyst which has aged for 168 hours has lost the majority of its activity. By contrast, the catalyst aged for 390 hours which has been regenerated with a cobalt compound returns to an activity which is substantially similar to that of a new catalyst.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. The process of stabilizing or regnerating the hydroformylation catalyst for propene, said catalyst consisting essentially of a catalytic complex of rhodium, carbon monoxide, and a triarylphosphine, comprising adding to said catalytic complex a cobalt compound free of any group which adversely affects the hydroformylation reaction.

2. The process of claim 1 wherein said cobalt compound is added to said catalytic complex prior to the hydroformylation reaction, during the hydroformylation reaction, or to the spent catalyst.

3. The process of claim 1 wherein said cobalt compound is added in an atomic ratio of Co/Rh of from 50/1 to 1/10.

4. The process of claims 1, 2, or 3 wherein the cobalt compound is selected from a carbonyl compound, an inorganic salt, an organic salt, or mixtures thereof.

5. The process of claims 1, 2, or 3 wherein the cobalt compound is dicobalt octacarbonyl.

6. In the process of hydroformylating propene with a catalytic complex consisting essentially of rhodium, carbon monoxide, and a triarylphosphine, the improvement comprising adding a cobalt compound to the reaction medium during the hydroformylation, said colbalt compound being free of any group which adversely affects the hydroformylation reaction.

7. The process of claim 6 wherein the cobalt compound is selected from a carbonyl compound, an inorganic salt, an organic salt, or mixtures thereof.

8. The process of claim 7 wherein the cobalt compound is dicobalt octacarbonyl.

9. The process of claims 6, 7, or 8 wherein the cobalt is added in an atomic ratio of Co/Rh of from 50/1 to 1/10.

* * * * *